US012625120B2

(12) United States Patent     (10) Patent No.:    US 12,625,120 B2

Thomas et al.              (45) Date of Patent:      May 12, 2026

(54) SYSTEMS, METHODS, AND DEVICES FOR MONITORING A GASEOUS OXIDIZING AGENT IN A DATA STORAGE DEVICE, AND RELATED SYSTEMS, METHODS, AND DEVICES

(71) Applicant: Seagate Technology LLC, Fremont, CA (US)

(72) Inventors: Patrick M. Thomas, Lyons, CO (US); Bijoyendra Nath, Minneapolis, MN (US); Roger J. Kassab, Aldie, VA (US); Scott R. Warmka, Burnsville, MN (US); Mark A. Gaertner, Minneapolis, MN (US); Abbas Ali, Prior Lake, MN (US)

(73) Assignee: Seagate Technology LLC, Fremont, CA (US)

( * ) Notice: Subject to any disclaimer, the term of this patent is extended or adjusted under 35 U.S.C. 154(b) by 302 days.

(21) Appl. No.: 18/374,398

(22) Filed: Sep. 28, 2023

(65) Prior Publication Data

US 2024/0110901 A1     Apr. 4, 2024

Related U.S. Application Data

(60) Provisional application No. 63/411,666, filed on Sep. 30, 2022.

(51) Int. Cl.
| | |
|---|---|
| *G01N 33/00* | (2006.01) |
| *G11B 33/14* | (2006.01) |
| *H05K 5/06* | (2006.01) |

(52) U.S. Cl.
CPC ......... *G01N 33/0062* (2013.01); *G11B 33/14* (2013.01); *H05K 5/06* (2013.01)

(58) Field of Classification Search
CPC ....... G01N 33/0062; H05K 5/06; G11B 33/14
See application file for complete search history.

(56) References Cited

U.S. PATENT DOCUMENTS

| | | | | |
|---|---|---|---|---|
| 6,144,178 A | * | 11/2000 | Hirano ............... | G11B 33/1486 |
| | | | | 318/476 |
| 6,646,821 B2 | * | 11/2003 | Bernett .............. | G11B 33/1486 |
| | | | | 360/99.18 |
| 7,062,387 B1 | * | 6/2006 | Burns ................ | G11B 33/1466 |
| | | | | 702/50 |
| 7,478,760 B2 | | 1/2009 | Beatty et al. | |
| 7,695,547 B2 | * | 4/2010 | Smith .................... | B01D 53/28 |
| | | | | 360/97.12 |
| 7,808,740 B2 | * | 10/2010 | Tanabe ................. | G11B 5/6064 |
| | | | | 360/75 |
| 8,094,409 B2 | | 1/2012 | Feliss et al. | |
| 9,570,114 B1 | * | 2/2017 | Sudo ...................... | H05K 5/069 |
| 11,024,343 B2 | | 6/2021 | Luebben et al. | |
| 11,340,677 B2 | | 5/2022 | Bimberg et al. | |

(Continued)

*Primary Examiner* — Steven L Yeninas
(74) *Attorney, Agent, or Firm* — Kagan Binder, PLLC

(57)           ABSTRACT

The present disclosure relates to devices, circuits, and methods of determining power consumption in an electronic device (e.g., HDD) so that the determined power consumption can be used to determine a concentration of the gaseous oxidizing agent component in an interior gas space of the sealed enclosure and/or actively supply gaseous oxidizing agent component to the interior gas space of the electronic device if the determined power consumption is below a threshold value.

20 Claims, 7 Drawing Sheets

(56) References Cited

U.S. PATENT DOCUMENTS

| | | | |
|---|---|---|---|
| 2009/0296271 A1* | 12/2009 | Feliss | G11B 33/148 |
| | | | 360/97.22 |
| 2021/0043233 A1* | 2/2021 | Luebben | G11B 33/022 |
| 2022/0406341 A1 | 12/2022 | Luebben et al. | |

* cited by examiner

SYSTEMS, METHODS, AND DEVICES FOR MONITORING A GASEOUS OXIDIZING AGENT IN A DATA STORAGE DEVICE, AND RELATED SYSTEMS, METHODS, AND DEVICES

RELATED APPLICATION

The present nonprovisional patent application claims the benefit of commonly owned provisional Application having Ser. No. 63/411,666, filed on Sep. 30, 2022, by Thomas et al., wherein said provisional Application is incorporated herein by reference in its entirety.

SUMMARY

The present disclosure includes embodiments of a method of monitoring the concentration of a gaseous oxidizing agent component in an electronic device, wherein the method includes:

- determining power consumption of one or more electrical components disposed in a sealed enclosure of the electronic device; and
- determining a concentration of the gaseous oxidizing agent component in an interior gas space of the sealed enclosure based on at least the determined power consumption and/or actively supplying gaseous oxidizing agent component to the interior gas space of the electronic device if the determined power consumption is below a threshold value.

The present disclosure also includes embodiments of n electronic device including:

- a sealed enclosure having an interior gas space;
- one or more electrical components disposed in the sealed enclosure;
- a power supply in electrical communication with the one or more electrical components of the electronic device; and
- circuitry in electrical communication with the power supply and configured to:
  - determine power consumption of at least one of the electrical components disposed in the sealed enclosure of the electronic device, and
  - determine a concentration of gaseous oxidizing agent component in the interior gas space of the sealed enclosure based on at least the determined power consumption.

The present disclosure also includes embodiments of an integrated circuit including circuitry configured to:

- measure power consumption of one or more electrical components, and
- control a power supply to supply power to a device to increase a concentration of gaseous oxidizing agent component in a sealed enclosure based on at least the measured power consumption.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The detailed description below makes reference to the following figures, wherein the same reference number may be used to identify the similar/same component in multiple figures. The schematic figures are for illustration purposes and are not necessarily drawn to scale.

DETAILED DESCRIPTION

Figure 1:
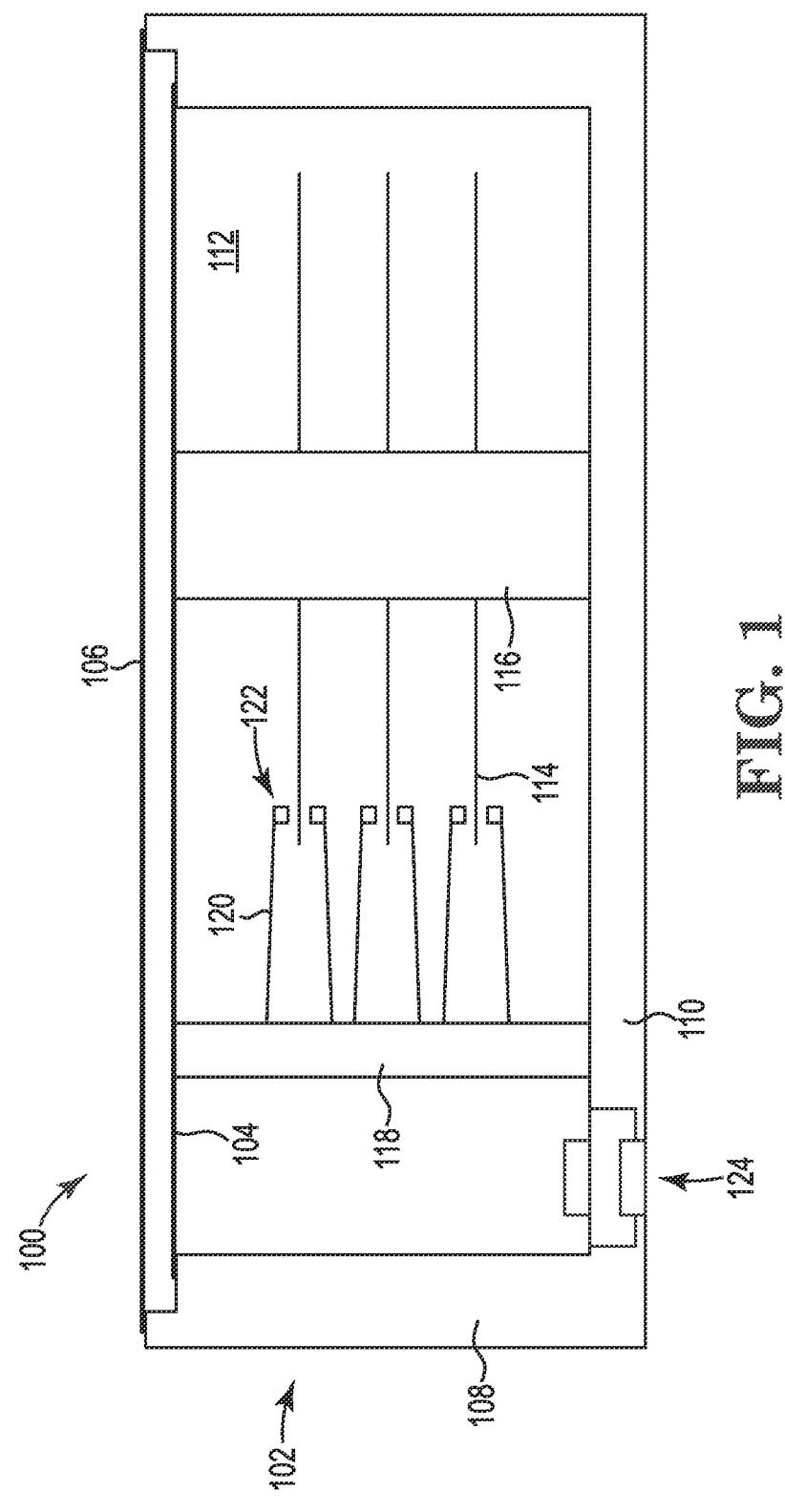
FIG. 1 shows a side cutaway schematic view of a non-limiting embodiment of an electronic device according to the present disclosure.

The present disclosure relates to electronic devices that include a sealed enclosure having an interior gas space, and one or more electrical components disposed in the sealed enclosure. In some embodiments, an electronic device is a data storage device. Non-limiting examples of data storage devices include hard disk drives (HDDs) (internal and/or external), network attached storage (NAS), and the like. Examples of hard disc drives are reported in U.S. Pat. No. 7,478,760 (Beatty et al.) and U.S. Pat. No. 7,695,547 (Smith), wherein the entireties of said patents are incorporated herein by reference.

In some embodiments, for desirable performance and reliability characteristics in disk drives an operating atmosphere can include an initial fill of a gas mixture that includes primarily helium gas and a second minor gas fraction of a gaseous oxidizing agent component (oxidizer) for the entire operational life of the drive. The purpose of the primarily helium environment is to reduce gas turbulence induced vibration of the drive's internal components to facilitate track follow capability across disk track widths of 100 nm or less. The second minor gas component, the gaseous oxidizing agent component can oxidize inorganic and/or organic materials and limit their accumulation on one or more components within the interior of an electronic device such as a hard disk drive as desired (e.g., to maintain one or more electronic components within the interior space in as-built conditions). Chemical reactions between the gaseous oxidizing agent component and inorganic and/or organic materials is believed to result in the formation of gaseous by-products that are free to transport away.

It has been observed that the concentration of oxygen contained in welded HDDs can unfortunately decrease over time. The rate of decrease of oxygen concentration can depend on a variety of factors such as one or more drive operating conditions. The loss of oxygen over time can be attributed to chemical reactions between oxygen and internal drive components. Such internal drive components include, but are not limited to, the recording media, activated carbon, and ferrous metal components. The measured rate of loss of oxygen is expected to result in the oxygen concentration dropping below a desired concentration over the service life of the HDD.

The interior gas space of an electronic device can include helium gas to maintain sufficient vibration mitigation. As the fraction of helium is decreased (e.g., from 100%), the vibrational performance of the drive mechanics can degrade, suggesting it can be beneficial to limit the non-helium oxidizing gas constituents to a minimum mole fraction as desired. In some embodiments, the helium gas is present in the interior gas space at a mole fraction of 99 percent or less based on the total gas in the interior gas space (e.g., from 80 to 99 percent, from 80 to 95 percent, from 85 to 95 percent, or even from 85-90 percent) and the remaining balance is oxygen.

The interior gas space of an electronic device can have a nominal relative humidity of 20% or less at 25° C., 15% or less at 25° C., 10% or less at 25° C., 5% or less at 25° C., or even 1% or less at 25° C.

In some embodiments, an electronic device can be a sealed electronic device, which can be defined by, e.g., the amount of gas that leaks from the electronic device after it has been sealed (e.g., a welded HDD). In some embodiments, the interior gas space includes helium gas and the electronic device is hermetically sealed such that it has a helium leak rate of $50\times10^{\wedge}-8$ atm (atmosphere) cc (cubic centimeter)/second or less at 25° C.; $20\times10^{\wedge}-8$ atm cc/second or less, $10\times10^{\wedge}-8$ atm cc/second or less; $5\times10^{\wedge}-8$ atm cc/second or less at 25° C.; or even $4.2\times10^{\wedge}-8$ atm cc/second or less at 25° C.

The present disclosure involves monitoring power consumption and using at least a portion of the power consumption information to infer the content of gaseous oxidizing agent component (e.g., oxygen content) within an interior space of a sealed electronic device such as a hard disk drive. If the content is too low, a device within the sealed enclosure can provide more gaseous oxidizing agent component to the interior space. As used herein, "a gaseous oxidizing agent component" includes one or more oxidizing agent species. Nonlimiting examples of oxidizing agent species include atomic oxygen, molecular oxygen, ozone, nitrous oxide, hydrogen peroxide, oxygen radical, dioxygen radicals, and mixtures thereof.

A non-limiting embodiment of an electronic device according to the present disclosure is described below with respect to FIG. 1.

FIG. 1 shows a cut away side view of a hard disk drive (HDD) 100, which represents an example of an electronic device according to the present disclosure. As shown in FIG. 1, HDD 100 includes a base deck 102, a process cover 104, and a final cover 106. The base deck 102 includes side walls 108 that, together with a bottom portion 110 of the base deck 102 and the process cover 104, create an interior gas space 112 that may house a plurality of data storage components like magnetic recording media 114, a spindle motor 116, a voice coil motor assembly 118, suspensions 120, and sliders 122 with read/write heads. The spindle motor 116 and the voice coil motor assembly 118 are shown in FIG. 1 as being coupled between the process cover 104 and the bottom portion 110 of the base deck 102.

In embodiments where the hard disk drive 100 incorporates heat-assisted magnetic recording (HAMR) technology, also referred to as energy-assisted magnetic recording (EAMR), thermally-assisted recording (TAR), thermally-assisted magnetic recording (TAMR), etc. In a HAMR device, a near-field transducer (NFT) concentrates optical energy into a tiny optical spot in a recording layer, which raises the media temperature locally, reducing the writing magnetic field required for high-density recording. A waveguide delivers light to the near-field transducer and excites the near-field transducer. During assembly of HDD 100, the process cover 104 can be coupled to the base deck 102 by removable fasteners and a gasket to seal a target gas (e.g., air, which includes nitrogen and oxygen, and a lower-density gas like helium) within the internal cavity 112. Once the process cover 104 is coupled to the base deck 102, a target "fill" gas may be injected into the interior gas space 112 through an aperture in the process cover 104, which can be subsequently sealed. Injecting the target gas may involve first evacuating existing gas from the internal cavity 112 using a vacuum and then injecting the target gas from a low-density gas supply reservoir into the internal cavity 112. Once the process cover 104 is sealed, the hard disk drive 100 can be subjected to a variety of processes and tests. When such processes and tests are complete, the final cover 106 can be coupled (e.g., welded) to the base deck 102.

The hard disk drive 100 can also include an electrical connector assembly 124 that facilitates communication of electrical signals to and from electrical components external to the hard disk drive 100 and electrical components positioned within the internal cavity 112.

Figure 2:
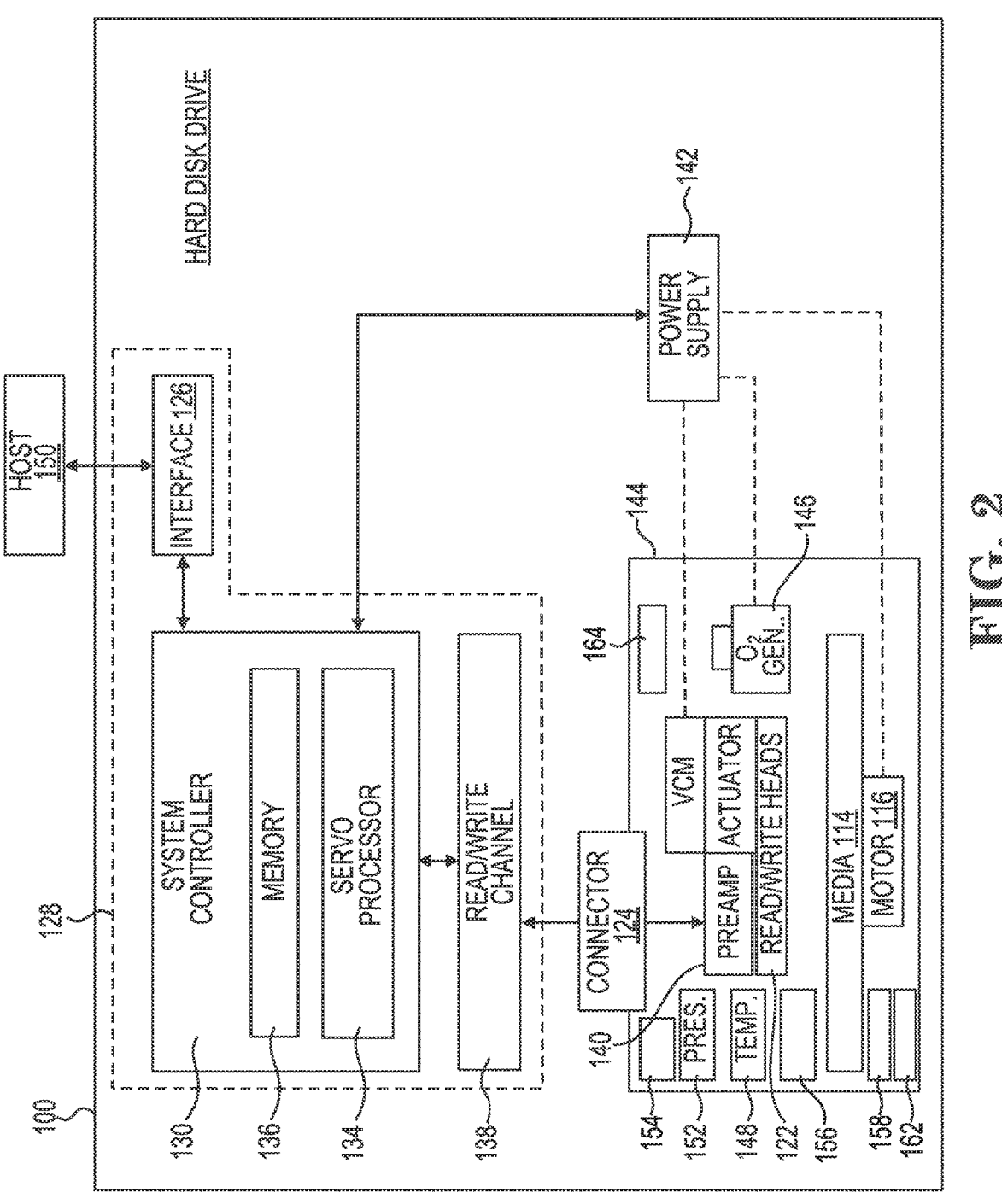
FIG. 2 shows a block diagram of a non-limiting embodiment of a data storage device such as a hard disk drive according to the present disclosure.

FIG. 2 shows a schematic of the hard disk drive 100 and some of its electrical components. As shown in FIG. 2, the hard disk drive 100 includes an interface 126 (e.g., an input/output interface) for transferring data to and from the hard disk drive 100. For example, the interface 126, among other features, can be communicatively coupled between a host 150 (e.g., a data storage system such as a server or laptop) and the read/write heads 122 to facilitate communication, using a standardized communication protocol (e.g., SATA, SAS, and the like), between the read/write heads 122 and the host 150.

The hard disk drive 100 can include a system-on-a-chip ("SOC") 128 (shown in dashed lines) that includes a system controller 130, which can include different modules such as a controller processor 132 (e.g., a microprocessor), a servo processor 134 (e.g., a microprocessor), and memory 136 coupled to the servo processor 134. The interface 126 may also be part of the SOC 128. The SOC 128 can also include a read/write channel 138, which encodes data associated with write commands and with read commands.

The SOC 128 may be an integrated circuit such as an application-specific integrated circuit ("ASIC") and field-programmable gate array ("FPGA") that includes instructions (e.g., in the form of firmware) for carrying out various functions of the hard disk drive 100. For example, the SOC 128 can include circuitry to control and carry out various aspects and methods of the hard disk drive 100 as described in more detail below. Although the interface 126, the system controller 130, etc., are shown as being part of a single SOC, the components and their functions can be distributed among several integrated circuits.

During operation, the hard disk drive 100 receives various data transfer commands (e.g., a read command or a write command) from the host 150. The data is encoded or otherwise processed by the read/write channel 138 and eventually stored to the magnetic recording media 114 via the read/write heads 122. Data associated with a read command may be retrieved from the magnetic recording media 114. Such data is then transferred to the host 150 by the interface 126. In some embodiments, the servo processor 134 controls operations of a pre-amplifier 140, which provides signals to the read/write heads 122 for writing magnetic transitions to the magnetic recording media 114 and for receiving signals from the read/write heads 122 in response to detecting magnetic transitions written to the magnetic recording media 114.

As shown in FIG. 2, the hard disk drive 100 includes a power supply 142, which can be controlled by the system controller 130. The power supply 142 supplies current to the motor 116, which rotates the magnetic recording media 114. The power supply 142 also supplies current to an actuator (e.g., a voice coil motor (VCM) assembly 116). The actuator is used to position the read/write heads 122 over a desired data track on the magnetic recording media 114 for data reading and data writing operations. For example, in response to a command to read data from or write data to a data track located at some distance away from where a respective read/write head 122 is currently positioned, a current may be supplied by the power supply 142 and applied to a voice coil of the VCM to rotate the actuator (and therefore the read/write head 122) towards the desired data track. The applied current through the coil generates a magnetic field that interacts with magnets of the VCM. The applied current may follow a current profile determined by and commanded by the servo processor 134. In some embodiments, the power supply 142 is an integrated circuit. For example, the power supply 142 may include a pulse-width-modulated-based current feedback amplifier driver circuit or transconductance amplifier driver circuit (e.g., either of which may comprise class D amplifier circuitry).

In addition to showing various electronic components of the hard disk drive 100, FIG. 2 shows that the hard disk drive 100 includes a sealed enclosure 144 in which, as shown in FIG. 2, many of the mechanical components of the hard disk drive 100 are positioned.

As indicated above, for some hard disk drives, it is desirable to maintain a minimum amount or percentage of gaseous oxidizing agent component in the sealed enclosure 144 over time. As such, the hard disk drive 100 can include features to monitor and control the content of gaseous oxidizing agent component in the hard disk drive's sealed enclosure 144.

As mentioned, an electronic device can include a power supply in electrical communication with the one or more electrical components of the electronic device and circuitry in electrical communication with the power supply. Hard disk drives can include circuitry that monitors various parameters of the hard disk drives and calculates, estimates, or measures power consumption of the various electrical components of the hard disk drive 100. In some embodiments, the determined power consumption can be used to determine a concentration of the gaseous oxidizing agent component in an interior gas space of the sealed enclosure and/or actively supply gaseous oxidizing agent component to the interior gas space of the electronic device if the determined power consumption is below a threshold value (discussed below).

Figure 3:
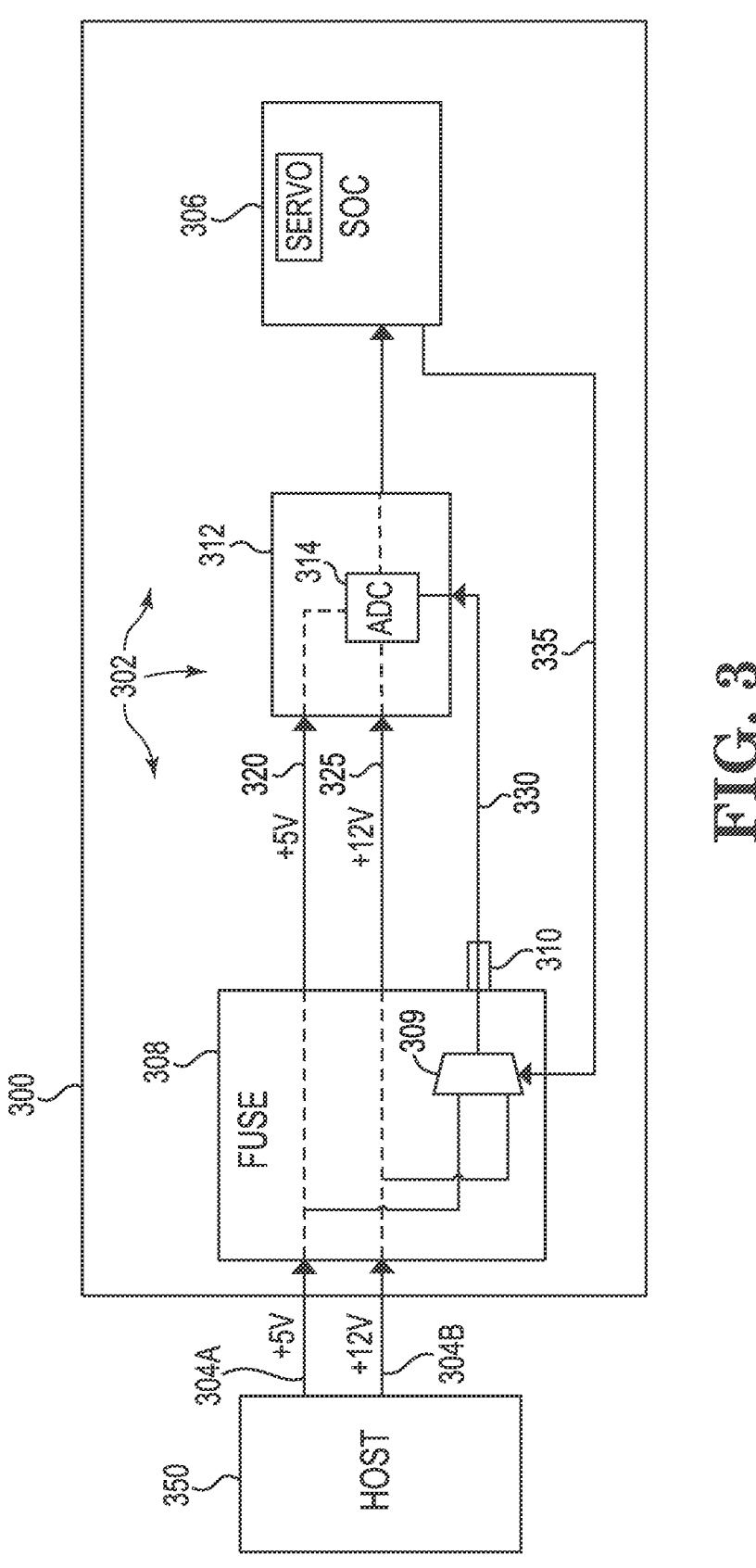
FIG. 3 shows a schematic of a non-limiting embodiment of a power monitoring circuit according to the present disclosure.

FIG. 3 and the description below depict and describe one approach for monitoring power consumption. It is appreciated that other approaches can be used to calculate, estimate, or measure power consumption in connection with controlling oxygen content in hard disk drives.

FIG. 3 shows a hard disk drive 300 with a power-monitoring circuit 302 (hereinafter referred to simply as the "circuit 302") that can be used to calculate the power usage of one or more electrical components in hard disk drive 300. As used herein, "electrical components" include electronic components (e.g., fuse 308 described below) and/or electro-mechanical components of an electronic device such as a HDD. Non-limiting examples of electronic components include electronics for reading/writing, for spinning one or more disks, for controlling various operations (e.g., read data, write data, transfer data between host and HDD, etc.), and the like. Non-limiting examples of electro-mechanical components include a spindle motor (e.g., a DC motor) to rotate a disk or disks and a voice coil motor assembly. A voice coil motor assembly includes voice coil motor and a head stack assembly that is used to re-position a read-write head on a desired data track. As explained below, circuit 302 is comprised of a sub-group of components on a printed circuit board assembly (PCBA). In some embodiments, the total power consumed by HDD 300 can be determined. In other embodiments, at least a portion of power consumed by one or more electrical components in HDD 300 can be monitored for a desired time period.

For simplicity of explanation, the hard disk drive 300 is not shown in FIG. 3 with all of the features described above with respect to the hard disk drive 100 of FIGS. 1 and 2 and vice versa. However, it is appreciated that the hard disk drive 300 could include each of the features shown and described with respect to the hard disk drive 100 of FIGS. 1 and 2. Further, the circuit 302 and its components can be incorporated into the hard disk drive 100.

In some embodiments, the circuit 302 includes features for measuring the voltage being inputted to the hard disk drive 300 and for measuring the current being consumed by the electrical components of the hard disk drive 300. As such, the measured voltage and current can be used to calculate, among other things, the power being used by one or more electrical components of the hard disk drive 300 (e.g., total power of the HDD at a given time or time period).

An electronic device according to the present disclosure can be in electrical communication with one or more power sources. Each power source can be the same or different from other power sources. As shown in FIG. 3, host 350 provides two power sources to HDD 300 (a first power source 304A and a second power source 304B). In some embodiments, the two power sources can have different voltages. For example, the first power source 304A can be a 5-volt power source and the second power source 304B can be a 12-volt power source. The first power source 304A can power components of the hard disk drive 300 such as SOC 306 and miscellaneous lower-power electrical components while the second power source 304B can power electro-mechanical components of the hard disk drive 300 such as the spindle motor, micro-actuators, and the voice coil motor assembly that rotates actuators coupled to the read/write heads.

In some embodiments, the circuitry includes a first component configured to receive at least one signal from the power supply and provide at least one signal indicative of current used by at least one of the one or more electrical components and a second component configured to calculate power consumption of the at least one electrical component based on the signal. In some embodiments, the first component includes a fuse in electrical communication with the power supply and configured to receive at least one signal from the power supply and provide an analog signal indicative of current used by at least one of the one or more electrical components. An example of such a fuse is shown in FIG. 3 as fuse 308. The signals from both the first power source 304A and the second power source 304B can be inputted to a fuse 308. The fuse 308 can be electrically coupled between an electrical connector and the rest of the electronics of the hard disk drive 300. As shown in FIG. 3, the first input voltage from the first power source 304A can be fed to power device 312 via 320 and the second input voltage from the second power source 304B can be fed to power device 312 via 325. The fuse 308 can be used to help prevent power from undesirably entering the hard disk drive 300 or leaking from the hard disk drive 300. For example, the electronics of the hard disk drive 300 may not be designed to handle low voltage levels. As such, the fuse 308 can help prevent voltage from flowing to the hard disk drive's electronics until the power reaches a threshold. This function can be helpful when power begins to ramp up when the hard disk drive 300 is initially turned on. As another example, in the event of a power loss of the hard disk drive 300, the fuse 308 can help prevent power within the hard disk drive 300 (e.g., power intended for emergency caching data or retracting the actuator in the hard disk drive 300) from leaking out of the hard disk drive 300 via the electrical connector.

In some embodiments, the fuse 308 is an intelligent electronic fuse (sometimes referred to as an "iFuse"), which is an integrated circuit with circuitry for carrying out the above-described functions. In some embodiments, the fuse 308 can be programmable such that the threshold (e.g., a voltage level threshold) at which it permits power to flow to electronics can be modified.

In some embodiments, the fuse 308 is only coupled to pins of the electrical connector that output power signals. For example, data commands and data-transferring signals may not pass through the fuse 308 and instead may be communicated directly between the electrical connector and an input/output interface of the hard disk drive 300.

In some embodiments, the fuse 308 is also configured to output an analog signal 330 that is indicative of the current being used by one or more electrical components of the hard disk drive 300. For example, the outputted analog signal 330 from the fuse 308 can be indicative of the current being used by (or drawn by) all or a portion of one or more electrical components powered by the first power source 304A and/or by all or a portion of one or more electrical components powered by the second power source 304B. In some embodiments, the outputted analog signal 330 has a voltage that is proportional to the current being used by one or more of the electrical components of the hard disk drive 300.

In some embodiments, as shown in FIG. 3, the fuse 308 includes only a single output pin 310. As such, the fuse 308 can be arranged to interleave respective signals indicative of the current being used by the electrical components powered by the first power source 304A (e.g., from the first input voltage) and by the electrical components powered by the second power source 304B (e.g., from the second input voltage). For example, as shown in FIG. 3, fuse 308 can include a MUX (multiplexer) circuit 309 that toggles which voltage power output will be monitored; the current of the 12V rail or the 5V rail, whichever is elected at the time of the reading. The MUX circuit 309 can receive a signal from the servo processor 134 of the SOC 128 to control the toggling of MUX circuit 309 between the 5V rail and the 12V rail.

In some embodiments, the output pin 310 includes or is coupled to a series resistor, which can be used to filter the outgoing signal by adjusting the gain or scaling of the respective signals indicative of the current being used by the electrical components powered by the first power source 304A (e.g., from the first input voltage) and by the electrical components powered by the second power source 304B (e.g., from the second input voltage). The filtered signal can then be measured.

In some embodiments, the analog signal 330 that is indicative of the current being used by one or more electrical components of the hard disk drive 300 is outputted from the fuse 308 and inputted to the power device 312.

In some embodiments, a circuit includes an analog-to-digital converter in electrical communication with the fuse and configured to convert the analog signal to a digital signal. An example of an analog-to-digital converter is shown in FIG. 3 as analog-to-digital converter 314, which is present as part of power device 312. In some embodiments, a second component includes a system-on-a-chip in electrical communication with the analog-to-digital converter and configured to calculate the power consumption of the at least one electrical component based on the signal. An example of a system-on-a-chip is shown in FIG. 3 as SOC 306. The analog-to-digital converter 314 of the power device 312 can convert the analog signal to a digital signal that can be used by the SOC 306. In some embodiments, the power device 312 includes a scaling module that scales down the amplitude of the signal being inputted to the SOC 306.

According to the present disclosure, the total power consumed by an electronic device (e.g., HDD) or a portion of one or more power sources (e.g., 12V power consumed by one or more electro-mechanical components such as a spindle motor and/or voice coil motor assembly) can be monitored/measured. Also, the power can be monitored at one or more discrete times, at one or more operating conditions, or continuously for a given time period. As one non-limiting example, referring again to FIG. 3, after receiving the digital signal indicative of the current being used by the electrical components of the hard disk drive 300, the SOC 306 uses the digital signal and the input voltage (e.g., 5 volts, 12 volts, or as measured by hardware of the hard disk drive 300) to calculate the actual power being used by the entire hard disk drive 300 (e.g., total power used of the hard disk drive 300). For example, the power can be calculated by multiplying the input voltage by the known current, which is based on the digital signal indicative of the current being consumed by the electrical components of the hard disk drive 300. In some embodiments, the input voltage 320 and/or 325 is measured by the analog-to-digital converter 314 of the power device 312. In some embodiments, SOC 306 includes a controller (e.g., via a servo processor) that calculates the power. For example, the servo processor may sample the measured voltages (320 and/or 325) and current 330 from the analog-to-digital converter 314 and then calculate power. The servo processor may, from a control path or signal path perspective, be located closest to the analog-to-digital converter 314 compared to other processors of the SOC 306. As described above, the SOC 306 can calculate the total power being consumed by electrical components of the hard disk drive 300 in real time by sampling the digital signal from the power device 312 and using the sampled or measured input voltages 320 and/or 325.

In some embodiments, other types of calculations can be made. For example, the SOC 306 can separately calculate the power being consumed by the electrical components powered by first power source 304A and the power being consumed by the electrical components powered by second power source 304B. The two power calculations can then be added together to calculate the total power usage of the hard disk drive 300.

In some embodiments, the power consumed by particular electrical components such as only the spindle motor and/or voice coil motor assembly (VCMA) can be measured at one or more times and one or more operating conditions. For example, the power draw of only a spindle motor and/or voice coil motor of a VCMA may be more reliably sensitive to changes in the molar ratio of oxygen to helium as compared to the power consumption of lower voltage components such as chips, etc. For example, the power draw of only a spindle motor may be more reliably sensitive to changes in the molar ratio of oxygen to helium as compared to the power consumption of lower voltage components because of the change in resistance between the surfaces of recording media and gas while the media is rotating, which impacts the power draw of the spindle motor. The resistance between the surfaces of recording media and gas while the media is rotating can vary due to changes in density of the gas (e.g., the density of the gas decreases as the content of oxygen decreases and the content of helium increases for a given set of other conditions). If desired, as mentioned above, total power may be monitored instead of individual electrical components. Even if the power consumption of a given electrical component does change with changes is oxygen concentration, the total power quantity will still change due to the change in power consumption of the electrical components that do change with changes is oxygen concentration.

The power consumption can be monitored according to the present disclosure for any desired time period and/or operating conditions that facilitate providing meaningful information. For example, power consumption information can be used include determining whether the concentration of gaseous oxidizing agent is too low so that one or more actions can be taken. Non-limiting examples of such actions include communicating to the host that device failure may be imminent so that one or more additional actions can be taken and/or so that the concentration of gaseous oxidizing agent component (e.g., oxygen) can be controlled as described herein. In some embodiments, the SOC 306 can calculate and timestamp the power usage. For example, minimum and maximum power usage over a time period can be determined. As another example, the SOC 306 can calculate average power usage across a given period of time (e.g., on the order of seconds to minutes to hours) that can initially be pre-determined and later adjusted (e.g., internally or by a command from the host 350). As yet another example, the power consumption at one or more times can be determined and compared to an initial power consumption value (e.g., when a HDD is manufactured) to estimate the concentration of oxygen within the HDD internal environment.

Power monitoring circuitry is also described in U.S. Pat. No. 11,340,677 (Bimberg et al.), which patent is hereby incorporated by reference in its entirety.

As mentioned above, the determined power consumption at a given set of conditions can be used to determine a concentration of the gaseous oxidizing agent component in an interior gas space of the sealed enclosure and/or actively supply gaseous oxidizing agent component to the interior gas space of the electronic device if the determined power consumption is below a threshold value. In some embodiments, the power consumed can be determined at one or more times for a given set of conditions that include spindle motor speed/operation (e.g., rotating or idling), VCMA operation (e.g., parked), temperature or temperature ranges of the interior gas space, among other operating parameters/conditions.

In some embodiments, the power consumption value that is determined while monitoring can simply be used as a proxy for concentration of gaseous oxidizing agent component (e.g., oxygen) and compared to a threshold value of power consumption to determine whether or not oxygen should be supplied to the interior gas space. For example, the measured power consumption of the hard disk drive 100 can be used as a proxy for the oxygen content of an oxygen/helium gas mixture within the sealed enclosure 144 of the hard disk drive 100. As the percentage of oxygen content is reduced over time, the hard disk drive 100 consumes less total power for a given set of operating conditions (e.g., motor speed, temperature). This is because helium is a lower density gas compared to oxygen so a higher percentage of helium in the hard disk drive 100 decreases power consumption. Given this relationship, the hard disk drive 100 can control (e.g., increase) its oxygen content within the sealed enclosure 144 based, at least in part, on the measured power consumption.

Figure 4:
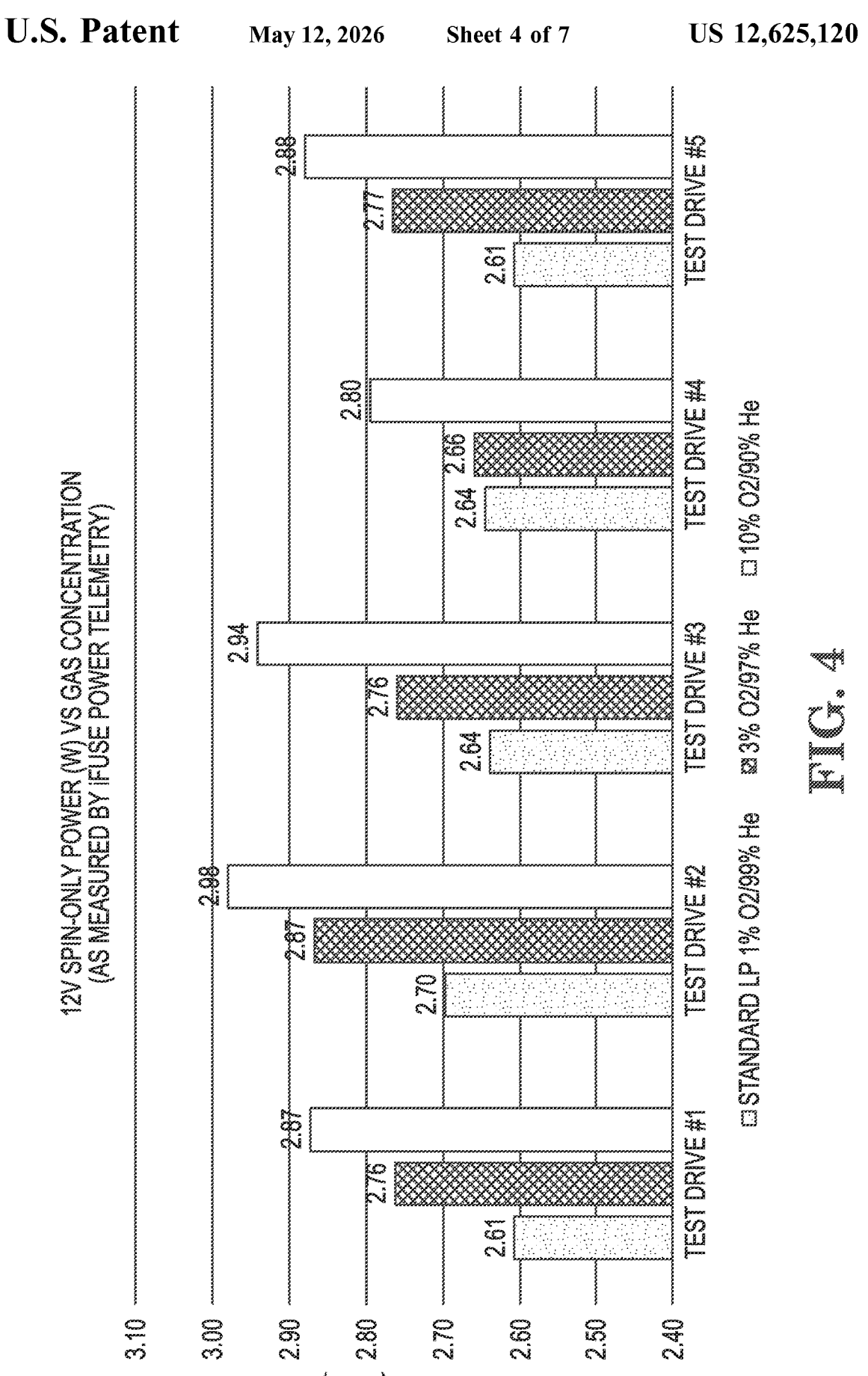
FIG. 4 shows a graph of empirical data of oxygen concentration versus spindle motor power consumption.

In some embodiments, the power consumption value that is determined while monitoring can also be used to determine a concentration of the gaseous oxidizing agent component in an interior gas space of the sealed enclosure, which can be compared to a threshold concentration value to determine whether or not gaseous oxidizing agent component (e.g., oxygen) should be supplied to the interior gas space. For example, if the measured power consumption is below a threshold, this may indicate that the oxygen content has lowered (and the helium content has increased) below a minimum threshold. According to the present disclosure, a correlation between determined power consumption of one or more electrical components and concentration of gaseous oxidizing agent. For illustration purposes, FIG. 4 shows that power consumption of a 12V power supply used for sealed hard disk drives decreases when the oxygen content of a helium/oxygen gas mixture decreases. The power was measured using iFuse power telemetry for a constant temperature and constant spindle motor speed among each sealed hard disk drive. Empirically determined data such as that shown in FIG. 4 can be used with a transfer function and can incorporate other inputs such as temperature measured by the temperature sensor 148 (shown in FIG. 2). The transfer function can take into account the fact that power consumption will depend on various operating conditions (e.g., motor speed, VCM activity, temperature) of the hard disk drive 100. The transfer function can then be used to determine oxygen concentration based, at least in part, on the measured power consumption, which can be used by control hardware/software to determine whether or not to supply oxygen to the internal gas space of a sealed hard disk drive. The transfer function can convert a measured amount of power consumption to an estimated percentage oxygen content. The estimated percentage oxygen content can then be compared to a threshold (e.g., a minimum desired amount of oxygen) to determine if the oxygen content is too low. In some embodiments, such a threshold can be set at, for example, 10% or less, 5% or less, 3% or less, 2% or less, or even 1% or less mole fraction of oxygen in the sealed enclosure 144.

In some embodiments, instead of comparing the amount of power consumption (or an estimated concentration of gaseous oxidizing agent component (e.g., oxygen content)) to a threshold power consumption (or threshold concentration gaseous oxidizing agent component (e.g., oxygen content)), an electronic device such as HDD 100 can detect rates of change of power and/or estimated concentration of gaseous oxidizing agent component (e.g., oxygen content) and compare those rates of change to a threshold rate of change, respectively.

As noted above, an electronic device such as hard disk drive 100 includes circuitry (e.g., integrated circuits such as the SOC 128, the power supply 142) to carry out various steps to monitor power use and/or monitor oxygen content, both of which can be used to control the oxygen content. In some embodiments, the routines (e.g., algorithms) for determining the amount of power consumption and determining whether the oxygen content should be increased are stored in the memory 136 and executed by the servo processor 134 of the SOC 128.

In response to determining that the concentration of the gaseous oxidizing agent component (e.g., oxygen content) is lower than desired (threshold value), an electronic device such as hard disk drive 100 can use a device disposed within the sealed enclosure and configured to actively supply (release and/or generate) gaseous oxidizing agent component to the interior gas space of the electronic device. For example, hard disk drive 100 can use the oxygen generator 146 to increase the amount of oxygen in the sealed enclosure 144. The oxygen generator 146 can include an element that, when heated, releases oxygen into the sealed enclosure 144 via a chemical reaction.

Figure 5:
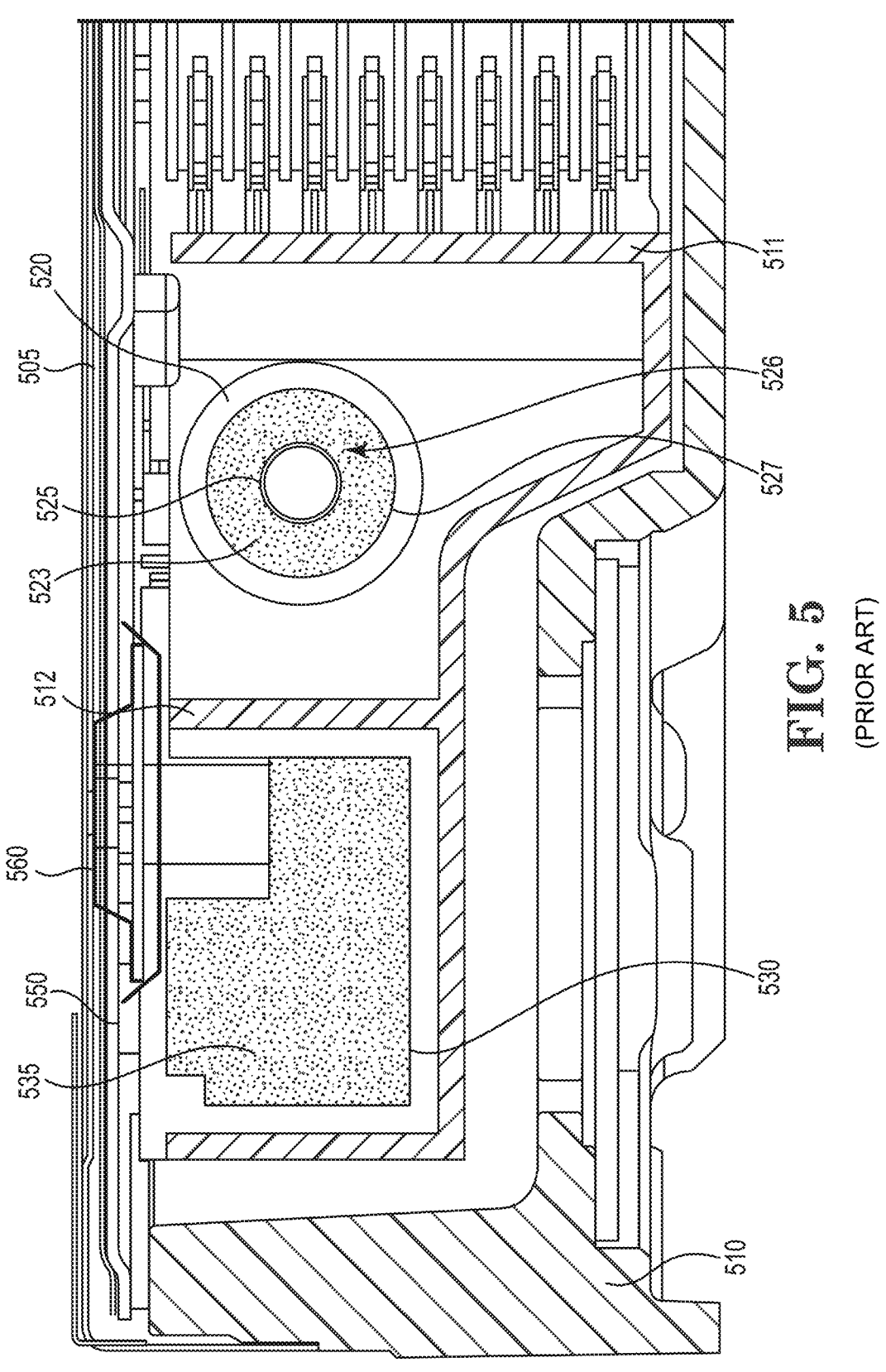
FIG. 5 illustrates a non-limiting embodiment of a device having a composition that can be actively controlled to generate a gaseous oxidizing agent component in a hard disk drive.

In more detail, a non-limiting example of a device that can actively generate gaseous oxidizing agent component is described in FIG. 5. FIG. 5 shows a close-up of a cross-sectional view through the environmental control module (ECM) 510 of an HDD with a top cover 505 installed. The ECM frame can anchor onto PCC Bulkhead (underneath the ECM) with pins. The ECM 510 contains desiccator 535 and a heater assembly 520 that includes a composition (e.g., zinc peroxide) that can generate a gaseous oxidizing agent component. Electrical power can be routed through the ECM frame from the PCC to the heater assembly 520. As discussed below, heater assembly 520 includes a helical heating coil and has a metallized, gas-tight seal to keep the composition (e.g., zinc peroxide) dry at least until use. The ECM 510 includes an ECM outer frame 511 and an inner wall 512 to separate the desiccator module 530 from the heater module 520. The inner wall 512 can help insulate the desiccator module 530 from the heater module 520 so that the desiccator module 530 is not heated to an undue degree, thereby causing moisture to transfer out of the desiccant 535. The ECM 510 is held in place vertically with the assistance of the top cover 505 gasket bead 550. The ECM 510 also includes a circular inlet diffuser filter 560 that aligns with a helium fill hole and filters incoming gas.

As shown in FIG. 5, the desiccator module 530 is a discrete unit that can slip fits into ECM frame 511 and inner wall 512. Alternatively, desiccator module 530 could be an integral with the ECM frame 511. As mentioned, desiccator module 530 contains desiccant for relative humidity (RH) control. Desiccator module 530 can also contain activated carbons for volatile organic compound (VOC) control.

As shown, the heater module 520 is in the form of a hollow cylinder having an outer wall 527 and an interior space 526 containing a helical heater coil 525. A composition 523 that can generate a gaseous oxidizing agent component (e.g., zinc peroxide) can be loaded into the interior space 526 so that the composition can be thermally heated by heater coil 525 as desired. The helical heater coil 525 is in thermal contact with the composition and the one or more heating elements are in electrical communication with a power supply. In some embodiments, the heating element is electrically coupled to a 5-volt or a 12-volt electrical power line.

The ECM 510 can include a breather membrane (e.g., polytetrafluorethylene (PTFE)) to allow diffusion of oxygen and other gasses while containing particle contamination. An example of a device that can actively generate gaseous oxidizing agent component is also described in U.S. Pat. No. 11,024,343 (Luebben et al.), which patent is hereby incorporated by reference in its entirety.

Figure 6:
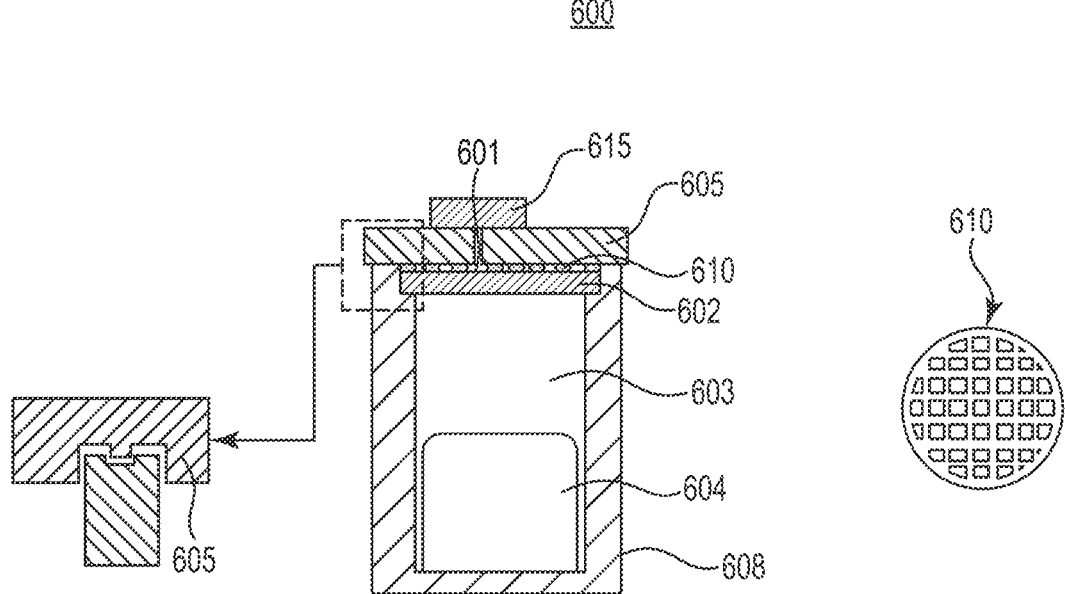
FIG. 6 shows a non-limiting embodiment of a dual chamber container with a permeation layer and micro-valve, which works like a 2-stage regulator; depicts a block diagram of steps of a method, in accordance with some embodiments of the present disclosure.

In some embodiments, hard disk drive 100 can use a device as shown in FIG. 6, which illustrates a non-limiting example of a dual chamber container 600 with a permeation layer and micro-valve, which works like a 2-stage regulator to increase the amount of oxygen in the sealed enclosure 144.

Container 600 includes a composition 604 that generates a gaseous oxidizing agent component. Alternatively, the container can be filled (and pressurized) with a gaseous oxidizing agent component (e.g., up to a pressure of 5-10 atm or more) to permit control led release of oxidizing agent component from container to the interior space of an electronic device (e.g., HDD) to provide oxidizing agent component in amount that maintains the concentration of the oxidizing agent component within a desired range over a desired time period.

As shown, the composition 604 is disposed in a relatively large chamber 603, where chamber 603 functions as an oxygen reservoir. Chamber 601 is a relatively small chamber compared to chamber 603 and functions to define a release volume. Chamber 601 is separated from chamber 603 via an oxygen permeable membrane 602 selected to equilibrate chambers 603 and 601 in about 1 minute to 30 days, and more preferably in 1 day to 15 days. A nonlimiting example of membrane 602 includes polyethylene. As shown, a grid 610 is positioned between membrane 602 and cap 605 to help avoid undue plastic deformation of 602 at temperature of about 60° C. Cap 605 can be fastened to housing 608 via welding or bonding (e.g., gluing with an adhesive). As shown, cap 605 is coupled to housing 608 along an interlocking bond line. Cap 605 also includes an electro-mechanical microvalve 615 (e.g., piezoelectric or bimetallic) that can be controllably actuated (e.g., electrically activated) from a closed position to an open position for release of oxygen from container 600.

Container 600 is small enough to fit within the cavity of an electronic device such as a hard disk drive or even inside and environmental control module. Container 600 can be constructed of non-elastic hard housing 608, which can help keep the interior of an electronic device clean.

As mentioned, container 600 functions like a two-stage regulator to equalize pressure from large chamber 603 to small chamber 301 like a tiny scuba tank (in a time period of hours or days). In some embodiments, oxygen can be released from small chamber 301 into the interior of an electronic device every 4-6 weeks. For example, about 1 cubic centimeter per week of oxygen can transfer from chamber 303 to chamber 301. Oxygen can be released from chamber 301 via valve 315 relatively fast. The valve leak rate can be selected to be as low as desired (e.g., about 0.1 cubic centimeter or less per month).

Optionally, in some embodiments, one or more sensors disposed within the sealed enclosure and configured to sense a physical parameter within the sealed electronic device. Non-limiting examples include at least one temperature sensor, at least one pressure sensor, at least one oxygen sensor, at least one thermal conductivity sensor, at least one electrochemical sensor, at least one optical sensor, at least one relative humidity sensor, and combinations thereof. A given sensor can be in electrical communication with the circuitry to facilitate estimating the concentration of gaseous oxidizing agent component in an interior gas space of a sealed enclosure. As shown in FIG. 2, in some embodiments, optional sensors that can be positioned in sealed enclosure 144 include temperature sensor 148, pressure sensor 152, oxygen sensor 154, thermal conductivity sensor 156, electrochemical sensor 158, optical sensor 162, and relative humidity sensor 164. Sensors for sensing physical parameters are also described in Pub. No. US 2022/0406341 (Luebben et al.), which published patent application is hereby incorporated by reference in its entirety. In some embodiments, using power consumption to estimate or as a proxy for the concentration of gaseous oxidizing agent component oxygen content eliminates the need for using one or more such sensors, if desired.

Figure 7:
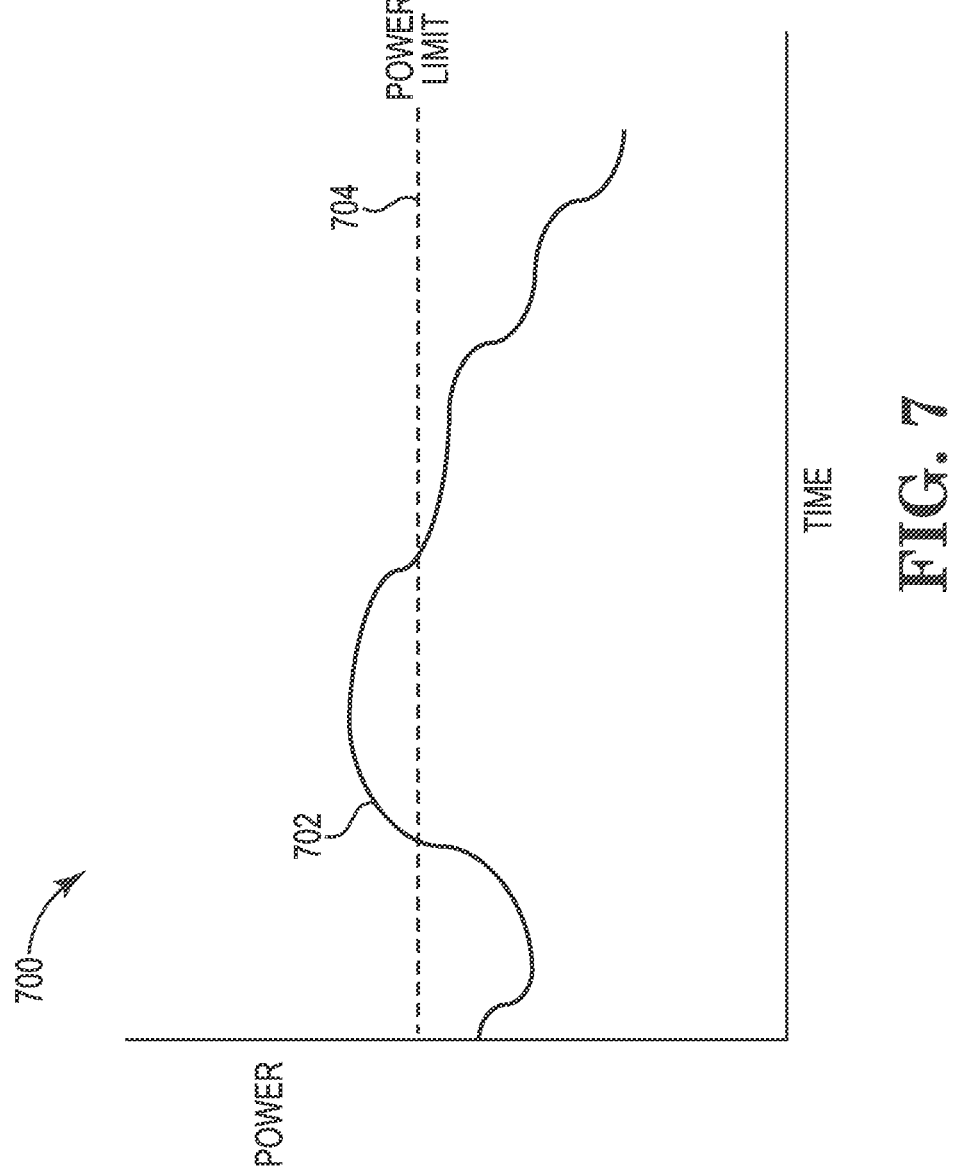
FIG. 7 shows a graph of power consumption over time.

A device for supplying gaseous oxidizing agent component such as oxygen to the interior gas space of an electronic device can be powered using any desired power source and any desired strategy for managing overall power of the electronic device. For example, regardless of how the content of gaseous oxidizing agent component is monitored, an electronic device (e.g., hard disk drive 100) may be unable to generate oxygen under some conditions due to limitation of power supply at a given time. For example, when the hard disk drive 100 is transferring (e.g., writing and/or retrieving) large amounts of data, the hard disk drive 100 may not be able to supply sufficient power to the oxygen generator 146 to produce oxygen without breaching power limits of the power supply 142. The circuitry for monitoring power can be used to determine whether the power supply 142 has available power to supply to the oxygen generator 146. FIG. 7 shows a graph 700 that with a plot 702 of real-time power consumption over time. The graph 700 also shows a power limit 704. In some embodiments, when the real-time power consumption approaches, reaches, or passes the power limit 704, the circuitry of the hard disk drive 100 can stop and/or block the power supply 142 from supplying power to the oxygen generator 146.

The power limit 704 can be determined based, at least in part, on the known power limit of the power supply 142 and the known power consumption of the oxygen generator 146. In some embodiments, the power consumption of the oxygen generator 146 can depend on environmental conditions and operational life of the oxygen generator itself. As such, the power consumption (or a transfer function) of the oxygen generator 146 can be determined empirically.

In other embodiments, instead of calculating available power, the hard disk drive 100 places limits on use of the power supply 142 such that power is reserved for the oxygen generator 146. For example, the hard disk drive 100 may limit how much overall power the other electrical components of the hard disk drive 100 can consume such that power is reserved for use of the oxygen generator 146. As one specific example, the hard disk drive 100 may limit the how much power is sent to the voice coil motor assembly for carrying our seek operations.

Various modifications and additions can be made to the embodiments disclosed without departing from the scope of this disclosure. For example, while the embodiments described above refer to particular features, the scope of this disclosure also includes embodiments having different combinations of features and embodiments that do not include all of the described features. Accordingly, the scope of the present disclosure is intended to include all such alternatives, modifications, and variations as falling within the scope of the claims, together with all equivalents thereof.

What is claimed is:

1. A method of monitoring a concentration of a gaseous oxidizing agent component in an electronic device, wherein the method comprises:

determining a power consumption of one or more electrical components disposed in a sealed enclosure of the electronic device; and determining the concentration of the gaseous oxidizing agent component in an interior gas space of the sealed enclosure based on at least the determined power consumption, and actively supplying the gaseous oxidizing agent component to the interior gas space of the electronic device if the determined power consumption is below a threshold value.

2. The method of claim 1, wherein the one or more electrical components are chosen from a spindle motor, a voice coil motor assembly, and combinations thereof.

3. The method of claim 1, wherein the determining the power consumption comprises:

providing a signal indicative of current being used by at least one of the one or more electrical components; and calculating the power consumption of the at least one electrical component based on the signal.

4. The method of claim 1, wherein determining the concentration of the gaseous oxidizing agent component in the interior gas space of the sealed enclosure based on at least the determined power consumption comprises comparing the determined power consumption of one or more electrical components to a previously determined correlation between the determined power consumption of one or more electrical components and the concentration of the gaseous oxidizing agent.

5. The method of claim 1, wherein the determining the concentration of the gaseous oxidizing agent component in the interior gas space of the sealed enclosure is based on one or more sensors i) disposed within the sealed enclosure and ii) configured to sense a physical parameter within the sealed enclosure, and wherein the one or more sensors are chosen from at least one temperature sensor, at least one pressure sensor, at least one oxygen sensor, at least one thermal conductivity sensor, at least one electrochemical sensor, at least one optical sensor, at least one relative humidity sensor, and combinations thereof.

6. The method of claim 1, further comprising:

comparing the determined concentration of the gaseous oxidizing agent component to a threshold concentration of the gaseous oxidizing agent component; and actively supplying the gaseous oxidizing agent component to the interior gas space of the electronic device if the determined concentration is below the threshold concentration of gaseous oxidizing agent component.

7. The method of claim 6, wherein the threshold concentration is 3 mole percent based on the total gas in the interior gas space.

8. The method of claim 1, wherein the gaseous oxidizing agent component comprises oxygen, and wherein the gaseous oxidizing agent component is present in a gaseous mixture with at least helium.

9. The method of claim 1, wherein the determining the power consumption comprises monitoring a signal from a power supply indicative of power delivered to the one or more electrical components.

10. An electronic device comprising:

a sealed enclosure having an interior gas space;

one or more electrical components disposed in the sealed enclosure;

a power supply in electrical communication with the one or more electrical components; and circuitry in electrical communication with the power supply and configured to:

monitor a signal from the power supply indicative of power delivered to the one or more electrical components, determine a power consumption of at least one of the electrical components disposed in the sealed enclosure of the electronic device based on the monitored signal, determine a concentration of a gaseous oxidizing agent component in the interior gas space of the sealed enclosure based on at least the determined power consumption, and actively supply the gaseous oxidizing agent component to the interior gas space if the determined power consumption is below a threshold value.

11. The electronic device of claim 10, wherein the one or more electrical components are chosen from a spindle motor, a voice coil motor assembly, and combinations thereof.

12. The electronic device of claim 10, wherein the circuitry comprises:

a first component configured to receive at least one signal from the power supply and provide at least one signal indicative of current used by at least one of the one or more electrical components; and a second component configured to calculate power consumption of the at least one electrical component based on the signal.

13. The electronic device of claim 12, wherein the first component comprises a fuse in electrical communication with the power supply and configured to receive the at least one signal from the power supply and provide an analog signal indicative of current used by the at least one of the one or more electrical components, further comprising an analog- to-digital converter in electrical communication with the fuse and configured to convert the analog signal to a digital signal, and wherein the second component comprises a system-on-a- chip in electrical communication with the analog-to-digital converter and configured to calculate the power consumption of the at least one electrical component based on the signal.

14. The electronic device of claim 10, further comprising one or more sensors disposed within the sealed enclosure and configured to sense a physical parameter within the sealed enclosure, wherein the one or more sensors are chosen from at least one temperature sensor, at least one pressure sensor, at least one oxygen sensor, at least one thermal conductivity sensor, at least one electrochemical sensor, at least one optical sensor, at least one relative humidity sensor, and combinations thereof, wherein each sensor is in electrical communication with the circuitry, and wherein the circuity is configured to determine the concentration of the gaseous oxidizing agent component in the interior gas space of the sealed enclosure based on the sensed physical parameter of each sensor.

15. The electronic device of claim 10, further comprising a device disposed within the sealed enclosure and configured to actively supply the gaseous oxidizing agent component to the interior gas space of the electronic device, wherein the circuity is configured to:

compare the determined concentration of the gaseous oxidizing agent component to a threshold concentration of the gaseous oxidizing agent component; and actively supply the gaseous oxidizing agent component to the interior gas space of the electronic device if the determined concentration is below the threshold concentration of the gaseous oxidizing agent component.

16. The electronic device of claim 15, wherein the device comprises a composition that is configured to generate the gaseous oxidizing agent component, wherein the gaseous oxidizing agent component is configured to be generated to provide the gaseous oxidizing agent component in the interior gas space at a mole fraction in the range from 0.1 to less than 20 mole percent based on the total gas in the interior gas space, wherein the composition is configured to actively generate the gaseous oxidizing agent component, and wherein the device is configured to actively cause the composition to generate the gaseous oxidizing agent component.

17. The electronic device of claim 16, wherein the device further comprises one or more heating elements in thermal contact with the composition, wherein the one or more heating elements are in electrical communication with the power supply, wherein the circuitry is configured to apply power to the one or more heating elements in an on/off manner according to a predetermined time interval to heat the composition to a temperature that causes the composition to decompose to generate the gaseous oxidizing agent component, and wherein the generating device is configured to be disposed within an environmental control module, wherein the environmental control module includes a gaseous oxidizing agent component permeable membrane to permit the gaseous oxidizing agent component to pass from inside to outside of the environmental control module.

18. The electronic device of claim 15, wherein the device comprises a container disposed within the sealed enclosure, wherein the container includes the gaseous oxidizing agent component, wherein the device is configured to allow the gaseous oxidizing agent component to controllably transfer from inside the container to the interior gas space of the housing, wherein transfer of the gaseous oxidizing agent component from inside the container to the interior gas space of the housing is actively controlled.

19. An integrated circuit comprising circuitry configured to:

monitor a signal indicative of power delivered to one or more electrical components disposed within a sealed enclosure, determine a power consumption of at least one of the electrical components based on the monitored signal, determine a concentration of a gaseous oxidizing agent component in the sealed enclosure based at least on the determined power consumption, and control a power supply to supply power to a device to increase the concentration of the gaseous oxidizing agent component in the sealed enclosure if the determined power consumption is below a threshold value.

20. The integrated circuit of claim 19, wherein the circuitry comprises a servo processor or a system-on-a-chip.

\* \* \* \* \*